United States Patent
Porter et al.

(10) Patent No.: US 11,375,736 B2
(45) Date of Patent: Jul. 5, 2022

(54) CORN PROTEIN PRODUCT HAVING DECREASED FREE SULFITE LEVELS AND METHOD FOR MANUFACTURING SAME

(71) Applicant: CARGILL, INCORPORATED, Wayzata, MN (US)

(72) Inventors: Michael A. Porter, Maple Grove, MN (US); Hadi Nayef Yehia, Beavercreek, OH (US); Guo-Hua Zheng, Centerville, OH (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/086,744

(22) PCT Filed: Mar. 24, 2017

(86) PCT No.: PCT/US2017/023988
§ 371 (c)(1),
(2) Date: Sep. 20, 2018

(87) PCT Pub. No.: WO2017/165748
PCT Pub. Date: Sep. 28, 2017

(65) Prior Publication Data
US 2019/0116851 A1    Apr. 25, 2019

Related U.S. Application Data

(60) Provisional application No. 62/312,798, filed on Mar. 24, 2016.

(51) Int. Cl.
*A23J 1/14*    (2006.01)
*A23L 7/10*    (2016.01)
(Continued)

(52) U.S. Cl.
CPC ............... *A23L 7/198* (2016.08); *A23J 1/006* (2013.01); *A23L 5/20* (2016.08); *A23L 5/23* (2016.08);
(Continued)

(58) Field of Classification Search
CPC .......... A23L 33/18; A23L 33/105; A23L 5/20; A23L 7/198; A23L 7/00; A23L 7/152;
(Continued)

(56) References Cited

U.S. PATENT DOCUMENTS 2,105,760 A    1/1938   Swallen
2,120,946 A    6/1938   Swallen
(Continued)

FOREIGN PATENT DOCUMENTS

CN    1899076 A     1/2007
CN    101560252 A   10/2009
(Continued)

OTHER PUBLICATIONS

JP-4750901-B2, Takahara J. et al. Machine Translation, English, Aug. 17, 2011 (Year: 2011).*

(Continued)

*Primary Examiner* — Hong T Yoo (57) ABSTRACT

Described herein is a corn protein product comprising greater than about 20% corn protein on a dry weight basis and a free sulfite concentration of less than 150 ppm on an as-is basis. Also disclosed herein is a method to obtain this corn protein product including the steps of providing a protein-rich stream derived from a wet corn milling operation, wherein the protein-rich stream comprises greater than 20% corn protein on a dry weight basis, and treating the protein-rich stream with an oxidant, preferably hydrogen peroxide.

12 Claims, 3 Drawing Sheets

(51) Int. Cl.
  *A23J 1/00* (2006.01)
  *A23L 5/20* (2016.01)
  *C07K 14/415* (2006.01)
(52) U.S. Cl.
  CPC ............ *A23L 5/276* (2016.08); *C07K 14/415* (2013.01); *A23V 2002/00* (2013.01); *A23V 2250/5482* (2013.01)
(58) Field of Classification Search
  CPC ...... A23J 1/12; A23J 1/14; A23J 1/006; A23J 3/346; A23J 3/14; A23J 1/142; A23J 3/32; C07K 14/415
  See application file for complete search history.

(56) References Cited

U.S. PATENT DOCUMENTS

| | | |
|---|---|---|
| 2,124,284 A | 7/1938 | Hans |
| 2,133,591 A | 10/1938 | Swallen |
| 2,156,928 A | 5/1939 | Swallen |
| 2,218,221 A | 10/1940 | Schopmeyer |
| 2,227,605 A | 1/1941 | Swallen |
| 2,360,381 A | 10/1944 | Walsh |
| 2,384,388 A | 9/1945 | Nicholas |
| 2,414,195 A | 1/1947 | Evans |
| 2,704,257 A | 3/1955 | De |
| 4,024,120 A | 5/1977 | Phillips |
| 4,108,847 A | 8/1978 | Creinin |
| 4,213,941 A | 7/1980 | Boomer |
| 4,265,925 A | 5/1981 | Campbell |
| 4,361,651 A * | 11/1982 | Keim ............... C12P 7/06 435/161 |
| 4,624,805 A | 11/1986 | Lawhon |
| 4,716,218 A | 12/1987 | Chen et al. |
| 5,254,673 A | 10/1993 | Cook et al. |
| 5,254,763 A | 10/1993 | Gill |
| 5,367,055 A | 11/1994 | Takahashi |
| 5,410,021 A | 4/1995 | Kampen |
| 5,498,431 A | 3/1996 | Lindner |
| 5,510,463 A | 4/1996 | Takahashi |
| 5,580,959 A | 12/1996 | Cook et al. |
| 5,602,286 A | 2/1997 | Muralidhara |
| 5,798,446 A | 8/1998 | Neumueller |
| 5,847,238 A | 12/1998 | Muralidhara |
| 6,169,217 B1 | 1/2001 | Cheryan |
| 6,433,146 B1 | 8/2002 | Cheryan |
| 6,602,985 B1 | 8/2003 | McInnis et al. |
| 6,610,831 B1 | 8/2003 | McInnis et al. |
| 6,846,909 B2 | 1/2005 | Mairal et al. |
| 7,045,607 B2 | 5/2006 | Cheryan |
| 7,829,680 B1 | 11/2010 | Sander |
| 8,795,760 B2 | 8/2014 | Lawton |
| 9,226,515 B2 | 1/2016 | Van et al. |
| 2001/0009040 A1 | 7/2001 | Duvick |
| 2002/0183490 A1 | 12/2002 | Cheryan |
| 2003/0066106 A1 | 4/2003 | Strissel et al. |
| 2003/0198725 A1 | 10/2003 | Cardenas |
| 2004/0009263 A1 | 1/2004 | Liu et al. |
| 2005/0008759 A1 | 1/2005 | Nie et al. |
| 2005/0064079 A1 | 3/2005 | Allen et al. |
| 2005/0074538 A1 | 4/2005 | Elder et al. |
| 2006/0057275 A1 | 3/2006 | Wu et al. |
| 2006/0182857 A1 | 8/2006 | Thorre |
| 2006/0240169 A1 | 10/2006 | Heydtmann et al. |
| 2007/0087101 A1 | 4/2007 | Gusek et al. |
| 2007/0172914 A1 | 7/2007 | Slabbekoorn et al. |
| 2008/0102502 A1 | 5/2008 | Foody et al. |
| 2008/0118626 A1 | 5/2008 | McWilliams et al. |
| 2009/0041901 A1 | 2/2009 | Elmusa et al. |
| 2009/0053368 A1 | 2/2009 | Fox et al. |
| 2009/0148589 A1 | 6/2009 | Fox et al. |
| 2009/0209423 A1 | 8/2009 | Slabbekoorn |
| 2009/0215990 A1 | 8/2009 | Cheryan et al. |
| 2010/0016554 A1 | 1/2010 | Cheryan |
| 2010/0159521 A1 | 6/2010 | Cirakovic et al. |
| 2010/0221387 A1 | 9/2010 | Cristianini et al. |
| 2010/0233756 A1 | 9/2010 | Sunvold et al. |
| 2012/0027890 A1 | 2/2012 | Cerne |
| 2013/0273219 A1 | 10/2013 | Baier |
| 2014/0123855 A1 | 5/2014 | Lawton et al. |
| 2014/0161962 A1 | 6/2014 | Boebel |
| 2014/0193547 A1 | 7/2014 | Brown et al. |
| 2014/0220217 A1 | 8/2014 | Brown et al. |
| 2014/0271928 A1 | 9/2014 | Rehage |
| 2014/0303348 A1 | 10/2014 | Lawton |
| 2014/0343259 A1 | 11/2014 | Bleyer et al. |
| 2014/0356510 A1 | 12/2014 | Schweizer et al. |
| 2015/0201647 A1 | 7/2015 | Fosdick et al. |
| 2016/0165932 A1 | 6/2016 | Armentrout |
| 2016/0286840 A1 | 10/2016 | Shane |
| 2019/0029295 A1 | 1/2019 | Mielgo Iza et al. |
| 2020/0236977 A1 | 7/2020 | Li |

FOREIGN PATENT DOCUMENTS

| | | | |
|---|---|---|---|
| CN | 101703146 B | 11/2011 | |
| CN | 102669406 A | 9/2012 | |
| CN | 103059116 A | 4/2013 | |
| CN | 103554278 A | 2/2014 | |
| CN | 104938763 A | 9/2015 | |
| CN | 105541982 A | 5/2016 | |
| EP | 0510537 A1 | 10/1992 | |
| EP | 0648078 A1 | 4/1995 | |
| EP | 2401920 A1 | 1/2012 | |
| EP | 2491794 A1 | 8/2012 | |
| EP | 3075259 A1 | 10/2016 | |
| EP | 3375290 A2 | 9/2018 | |
| FR | 2902607 A1 | 12/2007 | |
| JP | 5754564 A | 4/1982 | |
| JP | 63185998 | 8/1988 | |
| JP | 63185999 | 8/1988 | |
| JP | 2011097928 A | 5/2011 | |
| JP | 4750901 B2 * | 8/2011 | ............... A23J 3/14 |
| KR | 101409213 B1 | 6/2014 | |
| WO | 8809622 A1 | 12/1988 | |
| WO | 9112730 A2 | 9/1991 | |
| WO | 9312667 A1 | 7/1993 | |
| WO | 9844807 A1 | 10/1998 | |
| WO | 0150882 A2 | 7/2001 | |
| WO | 2005074704 A1 | 8/2005 | |
| WO | 2005091995 A2 | 10/2005 | |
| WO | 2007019227 A1 | 2/2007 | |
| WO | 2009155350 A1 | 12/2009 | |
| WO | 2014188567 A1 | 11/2014 | |
| WO | 2015004448 A1 | 1/2015 | |
| WO | 2015109276 A1 | 7/2015 | |
| WO | 2016154441 A1 | 9/2016 | |
| WO | 2017011625 A1 | 1/2017 | |
| WO | 2017040273 A3 | 4/2017 | |
| WO | 2017058501 A1 | 4/2017 | |
| WO | 2017081347 A2 | 5/2017 | |
| WO | 2017165748 A1 | 9/2017 | |
| WO | 2017165756 A1 | 9/2017 | |
| WO | 2017189322 A1 | 11/2017 | |
| WO | 2018058150 A1 | 3/2018 | |
| WO | 2018237030 A1 | 12/2018 | |
| WO | 2019028263 A2 | 2/2019 | |
| WO | 2019060179 A1 | 3/2019 | |
| WO | 2019060673 A1 | 3/2019 | |

OTHER PUBLICATIONS (International Standard ISO) Native starch—Determination of starch content—Ewers polarimetric method. ISO 10520. Sep. 1997.

Database WPI, Week 198219, Thomson Scientific, London, GB; AN 1982-38049E. XP002794657, & Jp S 57 54564 A (Nippon Shokuhin Kako KK), Apr. 1, 1982 (Apr. 1, 1982).

Wu, YV, et al., "Protein-Rich Residue from Corn Alcohol Distillation: Fractionation and Characterization", Cereal chemistry, vol. 58, No. 4, Apr. 1981, pp. 343-347.

Wu, Y, et al., "balancing of sulfur storage in maize seed", BMC plant biology, vol. 12, May 30, 2012, 77: abstract; p. 3, figure 1; p. 8, col. 1, paragraph 2, May 2012, 3, 8.

(56) References Cited

OTHER PUBLICATIONS

Phillips, R. Dixon, et al., "Corn Protein Concentrate: Functional and Nutritional Properties", Food Science, vol. 44, Issue 4 (Jul. 1979): pp. 1152-1155.
Lim, Ho-Soo, et al., "Comparison of four different methods for the determination of sulfites in foods marketed in South Korea", Food Additives & Contaminants: Part A, 3014, vol. 31, No. 2, 187-196, DOI: 10.1080/19440049.2013.857048.
Johansson, D, et al., "influence of surface lipids in commercial zein on microstructure and rheological properties of gluten-free dough", annual transactions of the nordic rheology society, vol. 20, 2012, pp. 247-251 p. 247, col. 1, paragraph 1; p. 247, col. 2, paragraph 4; p. 248, col. 1, paragraph 1; p. 248, figure 1, 2012, 247-251.
Inglett, GE, et al., "high-shear, jet-cooking, and alkali treatment of corn distillers' dried grains to obtain products with enhanced protein, oil and phenolic antioxidants", food science and technology international, vol. 16, No. 4, Jul. 9, 2010, pp. 297-308; abstract; p. 298, col. 1, paragraph 5; p. 298, col. 2, paragraph 2; p. 300, table 2, Jul. 2010, 297-308.
Hojilla-Evangelista, Mila P., et al., "Sequential Extraction Processing of High-Oil Corn", Cereal Chemistry, AACC International Inc., US, vol. 8, No. 6, Nov. 1, 2003 (Nov. 1, 2003), pp. 679-683, XP001185001, ISSN: 0009-0352.
Bryla, Marcin, et al., "Effects of pH and Temperature on the Stability of Fumonisins in Maize Products", Toxins 2017, 9, 88; doi:10.3390/toxins9030088.
Dombrink-Kurtzman, et al., "Effect of Nixtamalization (Alkaline Cooking) on Fumonisin-Contaminated Corn for Production of Masa and Tortillas", J. Agric. Food Chem., vol. 48(11): pp. 5781-5786, 2000.
Gomez, M. H., et al., "Changes in the Starch Fraction During Extrusion-cooking of Corn", Food Science, vol. 48, Issue 2 (Mar. 1983); pp. 378-381.
(Solvay Interox) "Hydrogen Peroxide Controlling reduced sulphur compounds" Mar. 2011; [retrieved May 25, 2017]. Retrived tan the Internet: <URL:http://www.solvay.com.au/en/binaries/Controlling%20reduced%20suphur%20species-202502.pdf>; p. 5, first paragraph and first molecular equation.
International Search Report dated Jun. 28, 2017 for PCT/US2017/023988 filed Mar. 24, 2017 (2 pages).
McNeillie, Alastair, and Juli Bieser. "Hydrogen peroxide uses for the year 2000." Food Processing Oct. 1993: 59+. Business Insights: Global. Web. Feb. 9, 2016.
Anderson, Timothy J., et al., "Development of New Method for Extraction of a-Zein tan Corn Gluten Meal Using Different Solvents", Cereal Chem. 88(4): 356-362.
Anderson, Timothy J., et al., "Zein Extraction from Corn, Corn Products, and Coproducts and Modifications for Various Applications: A Review", Cereal Chem. 88(2): 159-173, 2011.
Dickey, L.C., "Elhanolic Extraction of Zein from Maize", Industrial Crops and Products 13 (2001), Apr. 30, 2000. 67-76.
Lawton, John W, "Zein: A History of Processing and Use", American Association of Cereal Chemists, Inc., vol. 79. No. 1, 2002, 1-18.
Momany, Frank A., et al., "Structural Charecterization of a-Zein", Journal of Agricultural and Food Chemistry, 2008, 54, 543-547.
Sessa, David J., et al., "Improved Methods for Decolorizing Corn Zein", Industial Crops and Products 18 (2003), 2003, 55-65.

Shukla, Rishi, et al., "Zein: the industrial prolein from corn", Industrial Crops and Products 13 (2001). 171-192.
"The Corn Refining Process" 2 pages, downloaded from https://corn.org/wp-contentiuploads/2009/11/CornRefiningProcess.pdf (Year: 2009).
Anderson, "Detoxification of Aflatoxin-Contaminated Corn", Proc. Symp. held in Atlanta, Ga., Jan. 26-27, 1982. Soth. Coop. Ser. Bull. 279:87-90 (Year: 1982).
Anderson, R. A.; "Detoxification of Aflatoxin-Contaminated Corn", Cereal Chemistry, 55, 87-90, Jan. 31, 1978.
Anderson, Timothy James, "Extraction of zein from corn co-products", Master thesis, 2011, Food Science and Technology, Iowa State University, pp. i-v and 1-114.
Bookwalter Corn Distillers Grains and Other By-Products of Alcohol Production in Blended Foods II. Sensory, Stability, and Processing Studies, Cereal Chem. Vol. 61, No. 6, 1984, 509-513.
Burns TD et al: Fumonisin concentrations and in vivo toxicity of nixtamalized Fusarium verticillioides culture material: Evidence for fumonisin-matrix interactions, Food and Chemical Toxicology, Pergamon, GB, vol. 46, No. 8, Aug. 1, 2008 (Aug. 1, 2008), pp. 2841-2848, XP022939030, ISSN: 0278-6915, DOI: 10.1016/J.FCT.2008.05.017 [retrieved on May 29, 2008].
Cielab color space—Wikipedia; https://en.wikipedia.org/wiki/CIELAB_color_space; retrieved Oct. 5, 2019; 9 pages.
Gupta Ho et al: "Plant Foods for Human Nutrition 52: Processing of maize germ oil cake into edible food grade meal and evaluation of its protein quality", Plant Foods for Human Nutrition, vol. 52, Mar. 1, 1998 (Mar. 1, 1998), pp. 1-8, XP055808466, Retrieved from the Internet: URL:https://link.springer.com/content/pdf/10.1023/A:1008088822395.pdf>.
Hojilla-Evangelista Met Al: "Optimizing extraction of zein and glutelin-rich fraction during sequential extraction processing of corn", Cereal Chemistry, AACC International Inc, US, vol. 80, No. 4, Jan. 1, 1979 (Jan. 1, 1979), pp. 481-484, XP009092386, ISSN: 0009-0352, DOI: 10.1094/CCHEM.2003.80.4.481.
Hojilla-Evangelista MP et al: "Characterization of Protein Extracted From Flaked, Defatted, Whole Corn By the Sequential Extraction Process!", Journal of the American Oil Chemists Society, Springer, DE, vol. 69, No. 3, Mar. 1, 1992 (Mar. 1, 1992), pp. 199-204, XP000245384, ISSN: 0003-021X, DOI: 10.1007/BF02635886.
Johnson et al., "Optimizing Extraction of Zein and Glutelin-Rich Fraction During Sequential Extraction Processing of Corn", Cereal Chem. Vol. 80, No. 4, 2003, 481-484.
Parris Net Al: "Extraction and Solubility Characteristics of Zein Proteins From Dry-Milled Corn", Journal of Agricultural and Food Chemistry, American Chemical Society, US, vol. 49, No. 8, Aug. 1, 2001 (Aug. 1, 2001), pp. 3757-3760, XP001071383, ISSN: 0021-8561, DOI: 10.1021/JF0011790.
Paulson et al. (1984) Can. Inst. Food Sci. Technol. J. 17:202-208.
Reiners et al., "Corn Proteins: Potential for their Industrial Use" 58th Annual American Association of Cereal Chemists, 1973.
Selling et al: "The effect of extrusion processing on Zein", Polymer Degradation and Stability, Bark I NG, GB, vol. 95, No. 12, Dec. 1, 2010 (Dec. 1, 2010), pp. 2241-2249, XP027527379, ISSN: 0141-3910.
Sydenham et al. J. Agric. Food Chem. 1995, vol. 43, pp. 1198-1201 (Year: 1995).

* cited by examiner

CORN PROTEIN PRODUCT HAVING DECREASED FREE SULFITE LEVELS AND METHOD FOR MANUFACTURING SAME

CROSS-REFERENCE TO RELATED APPLICATIONS

This application is a national phase application of PCT/US2017/023988, filed Mar. 24, 2017, which claims the benefit of U.S. Provisional Patent Application 62/312,798 filed Mar. 24, 2016, each of which is hereby incorporated by reference in its entirety.

TECHNICAL FIELD

This disclosure relates to corn protein products having low free sulfite concentrations and methods of manufacturing the same.

BACKGROUND

Protein-rich streams (e.g. germ meal, gluten meal, corn protein concentrate (for example Empyreal® 75 corn protein concentrate) and corn protein isolate) derived from typical wet corn milling processes contain sulfite in the range of about 500 ppm to about 2000 ppm (as is basis) due to sulfite added to facilitate effective wet milling of corn. The added sulfite plays two major roles during wet milling of corn: firstly to cleave disulfide bonds in the storage protein matrix thereby loosening protein-starch entrapment to facilitate starch/protein separation; and secondly to control unwanted microbial growth during the entire wet milling process. Consequently, the mill protein streams contain a combination of free sulfite (in equilibrium with $SO_2$) and bound sulfite in the form of S-sulfocysteine.

With a movement towards cleaner food labels, there is a desire to reduce the free sulfite content in these protein-rich streams.

SUMMARY

Described herein is a corn protein product comprising greater than about 20% corn protein on a dry weight basis and a free sulfite concentration of less than 150 ppm on an as-is basis. Also disclosed herein is a method to obtain this corn protein product including the steps of providing a protein-rich stream derived from a wet corn milling operation, wherein the protein-rich stream comprises greater than 20% corn protein on a dry weight basis, and treating the protein-rich stream with an oxidant, preferably hydrogen peroxide.

DETAILED DESCRIPTION

Described herein is a corn protein product comprising greater than about 20% corn protein on a dry weight basis and a free sulfite concentration of less than 150 ppm on an as-is basis and methods of manufacturing the same.

Oxidation Reaction

A protein-rich stream derived from a wet corn milling process is first provided. The protein-rich stream may be, for example but not limited to, corn germ meal, corn gluten meal (including both pressed and solvent extracted meal), corn protein concentrate for example Cargill Empyreal®, or corn protein isolate, These protein-rich streams typically comprise free sulfite concentration in the range of about 300 ppm to 5000 ppm on an as-is weight basis. For certain food applications, it is desirable to reduce this free sulfite content. Further, these protein-rich streams typically comprise greater than 20% corn protein, and in many aspects greater than 50% corn protein, and in some aspects, greater than 85% corn protein on a dry weight basis.

The protein-rich stream is treated with an oxidant to obtain a corn protein product. Because sulfite is a reducing compound, oxidation treatments have been reported to reduce sulfite levels in various foods and beverages. However, the unique sulfite-protein interaction in wet corn milling presents a challenge in decreasing sulfite concentration in the protein-rich streams described herein. It shall be understood that the term "treatment" includes washing, blending, mixing, etc., the corn protein product with an oxidant. Such treatments can include chemical and enzymatic oxidation of the sulfite in aqueous, organic solvent or gas systems.

The oxidant described herein can be, for example but not limited to, hydrogen peroxide, ozone gas, air, sodium hypochlorite, a combination of potassium bromate and ethanol, catalase, peroxidase, or a combination thereof. In preferred aspects, the oxidant is hydrogen peroxide.

For the production of low-sulfite corn protein products, a range of hydrogen peroxide treatments can be applied depending on the effectiveness and/or applicability of each option and the final target of free sulfite in corn protein products. Two preferred aspects of hydrogen peroxide treatments are to either spray a hydrogen peroxide containing water onto the protein-rich stream during drum filtration or mix hydrogen peroxide with ethanol and add it to a wet cake in an extractor, where the $H_2O_2$-ethanol-water mixture and the ethanol-water solvent is predominantly removed by a subsequent separation such as drainage, decanting, centrifugation, filtration of other methods known to the art. Care is taken in the extractor-based approach to create solvent-peroxide solutions that are not dangerously reactive. In aspects of this invention, at least 1.8 moles and no more than 10 moles of oxidant is needed as part of the oxidation treatment to oxidize 1 mole of free sulfite in the protein-rich stream. In preferred aspects, the oxidation reaction may take a total of 10 minutes to 2 hours.

It is surprising that treating the protein-rich stream with an oxidant such as hydrogen peroxide does not degrade the protein structure (and therefore negatively impact the nutritional value of the protein or functional properties of the protein). Without being bound by any theory, it is believed that the hydrogen peroxide treatment quickly and selectively reacts with free sulfite and hydrogen peroxide is not consumed by other potential impurities (e.g., peroxidases, microbials, typtophans, tyrosine, etc.). It is also surprising that the process of sulfite oxidation works in a range of pH values and a variety of moderate temperatures.

Corn Protein Product

After treating the protein-rich stream with the oxidant, the resulting corn protein product comprises a free sulfite concentration of less than 150 ppm on an as-is basis. In preferred aspects, the free sulfite concentration is less than 100 ppm on an as-is basis, more preferably less than 75 ppm on an as-is basis, 40 ppm on an as-is basis, even more preferably less than 20 ppm on an as-is basis, and even more preferably less than 10 ppm on an as-is basis. Note that free sulfite concentration is measured by the Monier-Williams AOAC 990.28 method or ion-chromatography method of AOAC 990.30. Furthermore, any reference to "sulfite" described herein means free sulfite.

Further, the resulting corn protein product while it may comprise corn protein greater than about 20% on a dry basis, preferred aspects of the corn protein product comprises corn protein between about 55% and 95% on a dry weight basis or between about 90% and 98% on a dry weight basis.

Furthermore, it is also desirable that the corn protein product comprise less than 35% digestible carbohydrate on a dry weight basis.

End-Use Applications

Protein ingredients derived from corn wet milling are commonly used in feeding domestic animals for economic and companion purposes. The invention described here would allow the manufacture of lower sulfite animal feed products. Protein ingredients derived from corn are not widely used in human foods for a variety of reasons, one of which is the presence of sulfite at concentrations higher than commonly acceptable. The invention described here overcomes this limitation. Consequently, corn-derived protein ingredients with low free sulfite concentrations might be economically included in breakfast cereal, nutrition bar, bakery product and processed meat formulations, among other things.

EXAMPLES

Note for many of the examples, the specific free sulfite concentration of the raw material is unknown, but the value is typically between 500 and 900 ppm on an as is basis (approximately 800 to 1500 ppm on a dry solids basis).

Example 1

Treating the Alpha-Amylase-Treated Heavy Gluten Slurry (Empyreal® Slurry) with Hydrogen Peroxide Cargill Empyreal® slurry is first provided. The slurry is held at 77° C. in an enclosed container. The slurry contains 13% dry solids when measured using METTLER-TOLEDO HALOGEN moisture balance at 110° C. The slurry has a pH 5.3.

The Empyreal® slurry is used at as-is pH or adjusted to pH 7.3 (with 50% NaOH) before use. The slurries are vigorously hand-mixed for homogeneity before 40 g aliquots are added to 50-ml test tubes. Hydrogen peroxide solution (30% active hydrogen peroxide) is added to each test tube at dosages of 0 (control), 500 or 1000 ppm of active hydrogen peroxide on a total mass basis. The test tubes are inverted to ensure a thorough mixing in a hybridizer set at 75° C. Test tubes are removed after a 15-90 minute treatment and centrifuged at 4000 rpm at room temperature for 5 minutes.

For sulfite analysis, the supernatant (liquid portion) is further diluted with 0.05 M tris-buffer pH9.5 then analyzed by ion-chromatography according to AOAC 990.30. The solid portion is re-suspended with the addition of 20-ml 0.05 M tris-buffer pH9.5 at 37° C. in the hybridizer for 10 minutes then centrifuged at 4000 rpm for 5 minutes. The supernatant is directly used or further diluted as needed with the tris-buffer for sulfite analysis on ion-chromatography.

Figure 1:
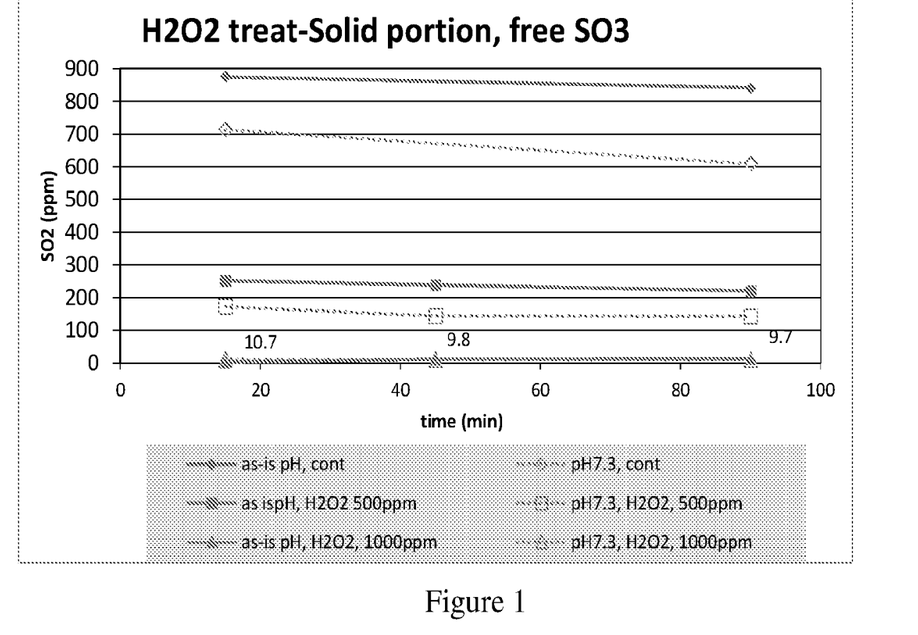
FIG. 1 shows the effect varying amounts of hydrogen peroxide has on free sulfite reduction in solid portions of an Empyreal® slurry according to Example 1.
Figure 2:
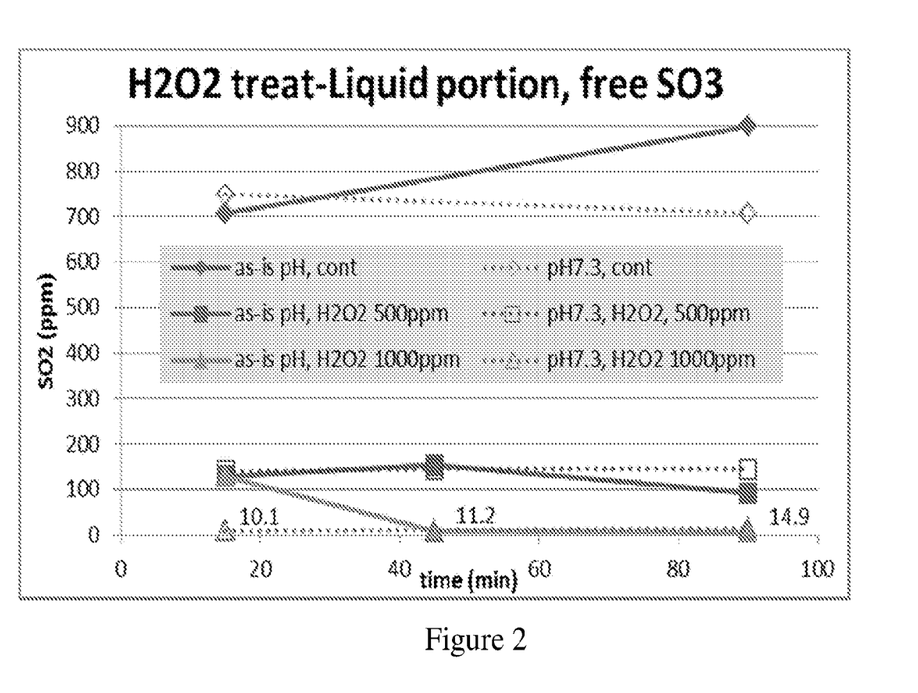
FIG. 2 shows the effect varying amounts of hydrogen peroxide has on free sulfite reduction in liquid portions of an Empyreal® slurry according to Example 1.

As shown in FIGS. 1 and 2, the starting Empyreal slurry material has about 900 ppm sulfite ($SO_3$). Data in FIGS. 1 and 2 also shows that treating Empyreal slurry with hydrogen peroxide effectively oxidized sulfite in both the solid portion and the liquid portion of the Empyreal slurry. When hydrogen peroxide is added at 1000 ppm, sulfite in both liquid and the solid portions is decreased to less than 20 ppm. The relatively consistent sulfite levels between 15 minutes and 90 minutes indicates that the hydrogen peroxide-sulfite reaction is effectively instantaneous and prolonged treatment time is not necessary.

Raising the pH seems to have a slight effect on sulfite oxidation in the solid portion when hydrogen peroxide dose is low at 500 ppm. No significant difference is found between pHs for the liquid portion or when enough hydrogen peroxide is added.

When calculated on a molar basis, 500 ppm hydrogen peroxide equals 14.71 mM and 900 ppm sulfite equals 11.25 mM. Data in FIGS. 1 and 2 show that the 14.71 mM hydrogen peroxide reduced about 9.375 mM sulfite in the liquid portion and about 8.125 mM sulfite in the solid portion. The efficacy of hydrogen peroxide from this data is about 64% for the liquid portion and 55% for the solid portion, respectively. This is likely due to reactions with a variety of inorganic and organic compounds contained in the slurry, including metals, lipids, and pigments. Dismutation would also eliminate some active hydrogen peroxide. Based on this data, a minimum of 1.8× moles of hydrogen peroxide is needed to get rid of 1 mole free sulfite in the solids consisting mainly of wet milled corn proteins.

Example 2

Treating the Alpha-Amylase-Treated Heavy Gluten Cake (Empyreal Cake) During Drum Filtration with Hydrogen Peroxide This laboratory experiment is conducted to mimic water washing of the wet cake during drum filtration operations. The wash ratio (WR) is calculated based on the ratio of washing solution to the original volume of the slurry. So a wash ratio of 1/10 indicates that 1 L of water is being used to wash the cake created from 10 kg of slurry. Because the washing occurs after the cake is essentially drained, the actual dilution of cake entrained water is much higher. In these experiments, the solids content of the Empyreal slurry is about 13%. Filter cakes moisture are about 60%, so 10 kg of slurry results in a cake containing less than 1300 g of solids and about 1950 mL of liquid. Subsequent washing with 1 L displaces about one-half of the entrained water in the cake. With a wash ratio of 1/25, the cake is washed with about 400 mL of liquid (or about 20% of the entrained water).

Cargill Empyreal® slurry is provided and maintained at 75° C. in a closed container until use. The slurry is vigorously hand-mixed for homogeneity before filtration. About 150 g of the well-mixed slurry is filtered through a filter paper with pore size of 40 micron (VWR Cat. No. 28313-068, 11.0-cm) under about 27-inches of Hg vacuum to yield a wet cake of about 3.2 mm (⅛ inch) thickness. When surface water disappears (takes about 1.5-2 minutes from the beginning of filtration), 6 ml (wash ratio=6/150=1/25 vol/wt) or 15 ml (wash ratio=15/150=1/10) city water containing 0 (control), 0.3% or 1.5% (0, 3000 and 15000 ppm, respectively) active hydrogen peroxide is sprayed to the surface of the wet cake using a spray gun at air pressure of about 15 psig while vacuum is kept on during the spray treatment. After all surface free moisture disappears, the cake is harvested.

The filtrates are used directly or diluted as needed with alkaline 0.05 M tris-buffer pH 9.5 for sulfite analysis with ion-chromatography. The wet cake (1 g) is fully resuspended with 10 ml of the tris-buffer at 37° C. for 30 minutes then centrifuged at 4000 rpm for 5 minutes. The supernatant was used directly or further diluted as needed with the alkaline tris-buffer for sulfite analysis on ion-chromatography (AOAC 990.30).

Figure 3:
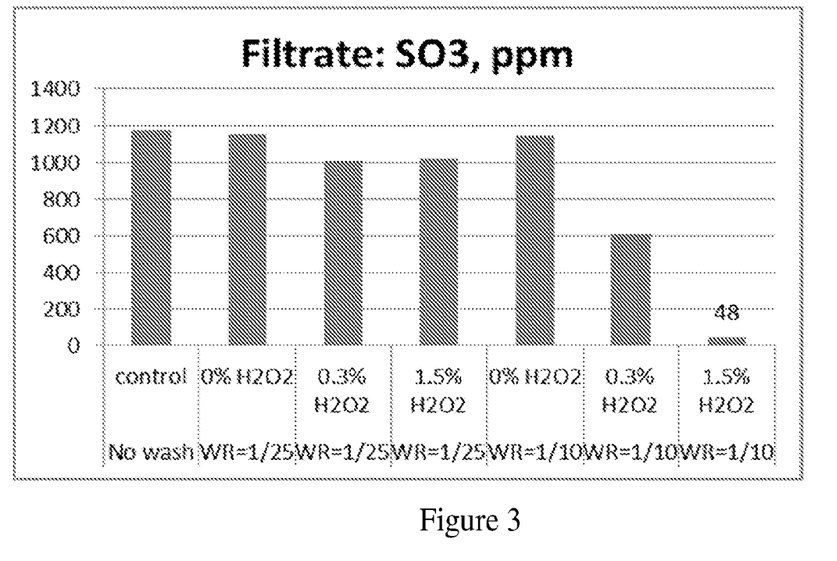
FIG. 3 shows the effect varying amounts of hydrogen peroxide has on free sulfite reduction in the filtrate of an Empyreal® wet cake according to Example 1.
Figure 4:
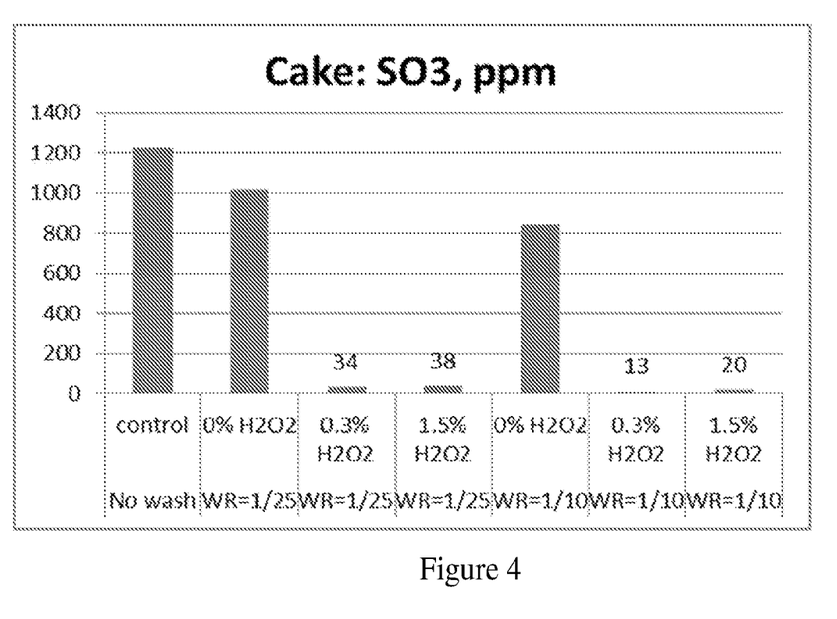
FIG. 4 shows the effect varying amounts of hydrogen peroxide has on free sulfite reduction in the cake portion of an Empyreal® wet cake according to Example 2.

This starting material has about 1200 ppm of free sulfite. Data in FIG. 3 shows that spraying city water containing hydrogen peroxide to wash the cake during filtration decreased sulfite in the cake to about 40 ppm at wash ratio of about 1/25 (peroxide-water vol/slurry wt) and further decreased to less than 20 ppm at higher wash ratio of 1/10.

It is noticed that at a lower wash ratio of 1/25, hydrogen peroxide concentration up to 1.5% does not cause significant change in sulfite levels in the filtrate. However, when wash ratio increased 2.5× to 1/10, sulfite in the filtrate is decreased about 50% to about 600 ppm when wash water contains 0.3% (3000 ppm) active peroxide. Sulfite in the filtrate is decreased to less than 50 ppm when the wash water contains 1.5% (15000 ppm) active peroxide and the wash ratio at 1/10. It is important to note that the filtered cake thickness is maintained to be ~⅛"-thick to simulate the drum-filtered cake thickness at plant scale. When ½"-thick cake is used in lab experiment, no reduction in filtrate sulfite was detected. However at plant scale, additional cracking of the drum-filtered cake can occur, which may lead to greater peroxide leaching into the filtrates and induce higher sulfite reduction in the filtrate.

Surprisingly, the peroxide treatment has a strong effect on the solids fraction and a smaller effect on the filtrate fraction. For corn wet milling operations, it is important that the sulfite level in the filtrate remains unchanged so that the filtrate can be recycled back to the mill Without being bound to any theories, it is believed that essentially none of the peroxide-containing solution passes through the filter cake into the filtrate (assuming no cake cracking). At 1/25, displacement of the entrained liquid is about 20% and at 1/10 it is about 50%. Assuming a starting concentration of 1200 ppm free sulfite in the slurry, 10 kg of slurry (containing 12,000 mg or 150 mmol) yields 3.25 kg of wet cake (containing 1.95 L of entrained solvent). The cake contains approximately 3900 mg of sulfite (at 81 g/mole, this represents about 48 milimoles) of sulfite in the cake. One liter of wash solution containing 0.3% active $H_2O_2$ (3000 mg/L at 34 g/mol) delivers 88 millimoles of peroxide for a molar ratio of oxidant-to-sulfite of about 1.8. About 6.75 kg of filtrate containing 8.1 g (or 100 mmol) of sulfite is removed by filtration before contact with peroxide. Thus filtration before peroxide treatment avoids three-quarters the peroxide that is otherwise required.

Example 3

Treating the Alpha-Amylase-Treated and Dewatered Heavy Gluten Cake (Empyreal Cake) During Ethanol Extraction with Hydrogen Peroxide Cargill Empyreal® slurry is provided and maintained at 75° C. in a closed container till use. 200 g of the well-mixed slurry is filtered through a filter paper with pore size of 40 micron (VWR Cat. No. 28313-068, 11.0-cm) under about 27-inches of Hg vacuum to yield a wet cake. When surface water disappears, 5 ml of city water is added to wash the cake (wash ratio=1/40) without breaking the vacuum. The resulting wet cake contains about 60% moisture when measured using METTLER-TOLEDO HALOGEN moisture balance at 110° C.

50 g of the wet cake is weighed into a 1-L glass Waring blender. After 200 ml of absolute ethanol containing 0 (control) or 0.15% (1500 ppm) active hydrogen peroxide (1 ml of 30% active hydrogen peroxide solution added into 200 ml ethanol) is added, the cake-ethanol mixture is blended at speed setting #1 (~3350 rpm) on Waring Commercial Laboratory Blender (Model HGB7WT$3) for about 1 minute. The well-blended mixture is immediately filtered through Whatman #4 filter paper under about 27-inches of Hg vacuum to yield a corn protein ingredient first extraction wet cake. The wet cake is dried in a vacuum oven at about 26 inches of Hg and 55° C. overnight. The dry product is ground in a coffee grinder before analysis for sulfite.

For sulfite analysis, 1 g of the ground sample is weighed into a 50-ml test tube then 10 ml of 0.05 M tris-buffer pH9.5 is added. The test tubes are inverted in a hybridizer at 50° C. for 30 min then centrifuged at 4000 rpm for 5 minute. The supernatant is directly used or further diluted as needed for sulfite analysis in ion-chromatography (AOAC 990.30). Results are expressed as $SO_2$ in ppm.

Figure 5:
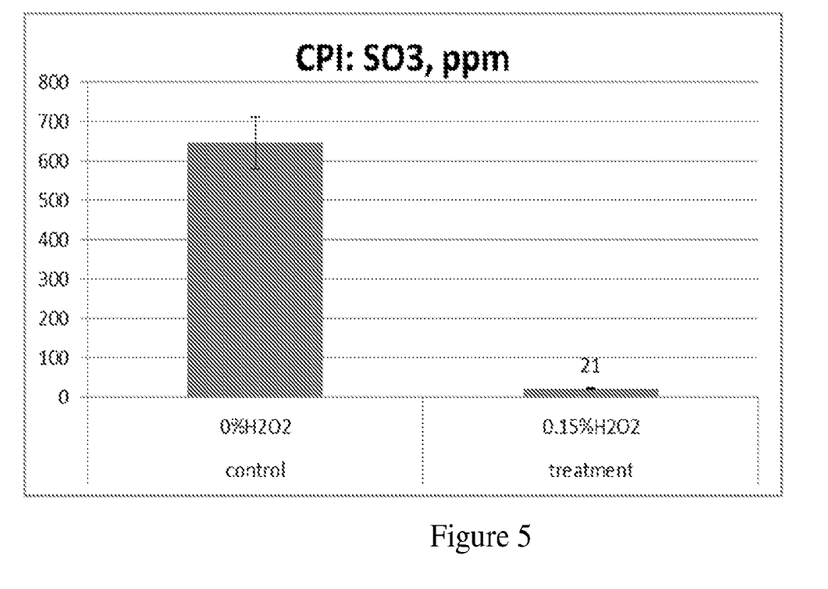
FIG. 5 shows the effect varying amounts of hydrogen peroxide has on free sulfite reduction of an Empyreal® wet cake according to Example 3.

The laboratory corn protein ingredient product made with the Empyreal cake extracted with 4 volumes of absolute ethanol (control) has an average of about 650 ppm sulfite, whereas the product made with 4 volumes of absolute ethanol containing 0.15% active hydrogen peroxide has about 20 ppm sulfite (FIG. 5). When calculated to molar basis, sulfite concentration in the Empyreal cake is about 8.1 mM whereas total active hydrogen peroxide concentration is about 176.5 mM, about 10 times the 1.8× minimum needed active hydrogen peroxide as stated above.

Example 4

Treatment on the Pilot Drum

Destarched corn gluten cake was collected on a rotary drum vacuum filter with rinsing. The destarched slurry was fed to the drum at 1.2 gal/min at a density of about 1.016 g/mL. The pH was as is, and estimated to be about 5.9 based on typical analysis of the filtered cake. The rinse water supplemented with active hydrogen peroxide at a concentration of 0.3% w/w was applied at 0.12 gal/min (Wash ratio=1/10). Upon completion of the vacuum dewatering, the treated cake was frozen until analysis.

10 kg of the peroxide-treated, destarched corn gluten cake with 60-65% moisture was processed through a dual rotor crusher with a 0.125-inch screen to generate a uniformly sized particle for homogeneous extraction. The cake was fed to a Crown Iron Works Model IV immersion extractor using a drag conveyor dropping through a crossover screw and then a delumper (for a better understanding, an illustration of the Crown Iron Works Model IV immersion extractor may be found on the crowniron.com website) into the extractor. The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent stream. At the end of the conveyor, the solids dropped onto another conveyor with a similar arrangement. The model IV extractor had six extraction stages. Fresh solvent was introduced at the discharge end and flowed towards the inlet end and was ultimately discharged at a point preceding the solids introduction. After the final solvent contact, the solids were conveyed up a long section to allow more extensive draining before falling into a crossover screw for transport to desolventizing. The solvent was fed into the system at different solvent:solids ratios of about 4 to about 18 and the solvent was maintained at different temperatures of about 20° C. to about 60° C. by in situ heat exchangers. Total contact time varied from about 30 to about 60 minutes.

The resulting materials were desolventized in a Bepex Solidaire dryer operated with a surface temperature of about 155-160° C. and an absolute pressure from about 270-330 millibar (with a target of about 300 millibar).

The desolventized material was ground in a hammer mill to yield a fine powder. As shown in Table 1, the resulting corn protein isolate products (all had greater than 85% protein on a dry weight basis) had 37 to 122 ppm $SO_2$, at least 80% decrease from the historical average $SO_2$ level of 530 ppm.

TABLE 1

Sulfite levels in corn protein isolate products according to Example 4

| Sample ID | Temperature C. | Solvent:solids ratio | Contact time min | $SO_2$ ppm as-is |
|---|---|---|---|---|
| CPI-P-102915-88 | 53.9 | 15.2 | 60 | 53 |
| CPI-P-103015-89 B | 60 | 17.4 | 60 | 37 |
| CPI-P-111715-96 A | 25 | 12 | 60 | 94 |
| CPI-P-111715-96 B | 25 | 4 | 60 | 91 |
| CPI-P-111915-97 | 42.5 | 8 | 45 | 88 |
| CPI-P-112315-98 A | 60 | 12 | 30 | 112 |
| CPI-P-112315-98 B | 60 | 12 | 60 | 98 |
| CPI-P-120115-100 | 60 | 4 | 30 | 102 |
| CPI-P-120715-102 12 | 25 | 4 | 30 | 92 |
| CPI-P-120915-103 14 | 60 | 4 | 30 | 122 |
| CPI-P-121115-104 15 | 25 | 12 | 30 | 77 |

Example 5

Treating a Wet Corn Protein Concentrate with Ozone Gas

An ozonation apparatus was assembled and placed in a fume hood. Approximately 100 grams of a wet Empyreal cake was weighed and placed in the column. The sample was lightly pressed in the column with a steel rod. The ozone generator was then turned on and allowed to build pressure for 2 minutes. The flow rate was then set to 3 LPM, but varied according to the packing and overall system pressure. The percentage dial down of ozone stream was set to 30% which generates 1.2 g/hr of ozone (resulting in a gaseous concentration in the 2000-ppm range). The ozone/oxygen mixture was passed through the bottom of column for 2.5, 5, 10, and 30 minutes. Residual ozone leaving from the top of column was bubbled through a 2% sodium bisulfite solution (SBS) to reduce and capture escaping ozone. Any remaining ozone dissipated into the air via the ventilation hood exhaust. At the end of each test run, the samples were analyzed for moisture content using a METTLER-TOLEDO HALOGEN moisture balance at 110° C. For sulfite analysis, the samples were extracted with 50 mM tris-buffer containing 5 mM EDTA at sample-to-buffer ratio of 1-to-10 at 37° C. for 10 min, followed by centrifugation at 4000 rpm for 5 min. The resulting supernatant was either directly analyzed or further diluted with the tris-buffer. Sulfite was analyzed in a ion-exchange chromatography (AOAC 990.30).

Figure 6:
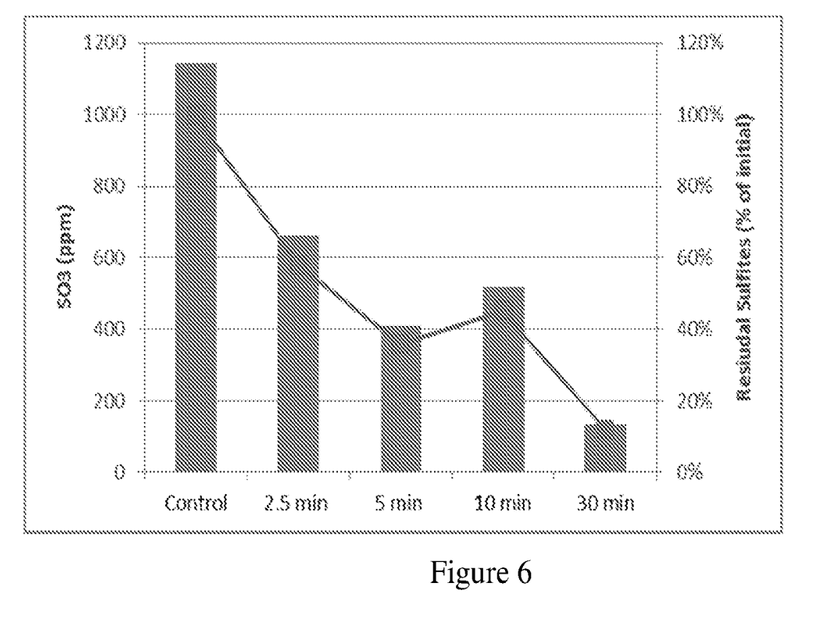
FIG. 6 shows the effect of ozonation on the decrease of free sulfite in Empyreal wet cake according to Example 5.

As shown in FIG. 6, the Empyreal cake (62% moisture) showed a significant decrease in sulfite content after treatment with ozone gas. The decrease reached 88.2% at 30 min of treatment.

Example 6

Treating Empyreal Slurry with Air

Cargill Empyreal slurry was provided. About 100 g of the slurry was transferred to a 150 ml jacketed glass column (25 mm×300 mm, Ace Glass) fitted with 100 micron filter discs on both ends. Compressed air was passed through the slurry at a flow rate of about 3 ml/sec from the bottom of the columns while the column jacket temperature was kept at 60° C. After 2.5 hour of air treatment, the slurry was filtered with filter paper (40 micron openings) to yield a wet cake of about 60% moisture. A similar cake was also obtained from untreated slurry (the control). Both wet cakes were dried in a vacuum oven dryer at about 26 inches vacuum and 55° C. overnight. The dry samples were ground in a coffee grinder to fine powders. For sulfite analysis, the samples were extracted with 50 mM tris-buffer containing 5 mM EDTA at sample-to-buffer ratio of 1-to-10 at 37° C. for 10 min, followed by centrifugation at 4000 rpm for 5 min. The resulting supernatant was either directly analyzed or further diluted with the tris-buffer. Sulfite was analyzed in an ion-exchange chromatography (AOAC 990.30).

Results showed that the control contained 266 ppm sulfite while the air-treated material had 204 ppm sulfite. The air treatment resulted in about 23% sulfite decrease in this case.

Example 7

Treating Empyreal Slurry with Sodium Hypochlorite

Cargill corn gluten meal slurry was provided. About 200 g of the heavy gluten slurry was weighed into a 500-ml polyethylene container followed by addition of appropriate amounts of sodium hypochlorite solution (Clorox Ultra containing 6.15% NaCl) so that NaClO concentration in the slurry were at 500 ppm (6.76 mM), 1000 ppm (13.52 mM) or 2000 ppm (27.04 mM) respectively. The bottles were placed in a shaking water bath at 130° F. for 15 mM before the contents were filtered through Whatman #4 filter paper to yield wet cakes of about 60% moisture. Separately, the heavy gluten slurry without sodium hypochlorite was filtered through Whatman #4 filter paper to yield a control cake. All wet cakes were dried in a vacuum oven at about 26 inches vacuum and 55° C. overnight. The dry material was ground to fine powder in a coffee grinder. The ground material was analyzed for sulfite concentrations using the Monier-William's procedure of distillation and volumetric titration (AOAC 990.28).

Results showed that the sodium hypochlorite treatment decreased sulfite by 45-90% (Table 2).

TABLE 2

Sulfite decrease by sodium hypochlorite treatment of heavy gluten slurry

| NaClO concentration | Sulfite as $SO_2$, ppm | Residual $SO_2$ as % of initial |
|---|---|---|
| 0 ppm (control) | 557 | 100% |
| 500 ppm | 307 | 55% |
| 1000 ppm | 121 | 22% |
| 2000 ppm | 58 | 10% |

Example 8

Treating Empyreal Wet Cake with Potassium Bromate and Ethanol

About 50 g of Empyreal wet cake was weighed into a 1-L glass Waring blender then potassium bromate was added at 0.2% or 1% levels on a cake dry solid basis. After 200 ml of absolute ethanol was added, the cake-potassium bromate-ethanol mixture was blended at speed setting #1 on Waring Commercial Laboratory Blender (Model HGB7WT$3) for about 1 min. The well-blended mixture was immediately filtered through Whatman #4 filter paper under about 27-inches vacuum to yield a CPI (corn protein isolate) wet cake. Control was obtained by the same ethanol treatment without the addition of potassium bromate. The cake was dried in a vacuum oven at about 26 inches and 55° C. overnight. The dry product was ground to fine powders in a coffee grinder. The fine powders were analyzed for sulfite concentrations according to Monier-William's AOAC procedure (990.28).

Results showed that potassium bromate at 0.2% and 1% decreased sulfite concentrations in the final corn protein isolate by 62% and 78% respectively (Table 3).

TABLE 3

Sulfite reduction by potassium bromate treatment of Empyreal wet cake in combination with ethanol to produce corn protein isolate

| Potassium bromate concentration | Sulfite as $SO_2$, ppm | Residual $SO_2$ as % of initial |
|---|---|---|
| 0 (control) | 580 | 100% |
| 0.2% dwb | 218 | 38% |
| 1% dwb | 128 | 22% |

Example 9

Treating a Corn Protein Isolate by Dry Blending with Calcium Peroxide

A corn protein isolate containing 92.3% protein on a dry weight basis (5.7% loss on drying) was produced in a pilot plant in Savage, Minn. Aliquots of about 5 g of the CPI product were weighed into 50-ml test tubes with screw caps. Calcium peroxide was added at concentrations of 0 (control, no calcium peroxide addition), 2170 ppm, 3300 ppm or 5080 ppm on a dry weight basis. The dry blend of calcium peroxide and CPI were further gently mixed by inverting the test tubes at ambient temperature for 1 week. Sulfite concentrations were analyzed according to Monier-Williams AOAC procedure (990.28).

Results showed about 76-78% sulfite reduction by dry blending calcium peroxide with the corn protein isolate (Table 4).

TABLE 4

Sulfite reduction by dry blending calcium peroxide with a corn protein isolate

| Calcium peroxide concentration | Sulfite as $SO_2$, ppm | Residual $SO_2$ as % of initial |
|---|---|---|
| 0 ppm (control) | 612 | 100% |
| 2170 ppm | 148 | 24% |
| 3300 ppm | 145 | 24% |
| 5080 ppm | 136 | 22% |

Example 10

Treating Empyreal Gluten Slurry with Catalase or Peroxidase

Heavy corn slurry was provided. About 100 g aliquots of the well agitated material containing 13% dry solids and greater than 80% protein on a dry weight basis were dispensed into 250-ml polypropylene bottles with screw-caps. Catalase (Catazyme L25, Novozymes) was added to the test tubes at 0 (control), 0.1% or 1% (v/w) levels while peroxidase (from horseradish, Sigma-Aldrich) was added at 0.1% or 0.3% (w/w) levels based on dry solids of the slurry. The bottles were placed in an orbitally shaking incubator set at 60° C. and 120 rpm. After 2 hours incubation, the slurries were filtered through 40 micron paper filters to yield wet cakes of about 60% moisture. The wet cakes were dried in a vacuum oven dryer at about 26 inches vacuum and 55° C. overnight. The dry samples were ground to fine powders in a coffee grinder. The fine powders were analyzed for sulfite according to the Monier-William's AOAC procedure (990.28). Results showed that the catalase treatment decreased sulfite by 25% and 38% at 0.1% and 1% enzyme dosages while peroxidase decreased sulfite by 15% and 29% at enzyme dosages of 0.1% and 0.3% respectively (Table 5).

TABLE 5

Sulfite decrease by catalase or peroxidase treatment of Empyreal gluten slurry to produce corn protein concentrate

| Enzyme | Dosage | Sulfite as $SO_2$, ppm | Residual $SO_2$ as % of initial |
|---|---|---|---|
| None | 0% (control) | 820 | 100% |
| Catazyme L25 | 0.1% v/dwb | 612 | 75% |
| | 1% v/dwb | 513 | 62% |
| Horseradish peroxidase | 0.1% w/w dwb | 698 | 85% |
| | 0.3% w/w dwb | 586 | 71% |

Example 11

Hydrogen Peroxide Treatment in the Pilot Extraction

Destarched corn gluten cake was collected on a rotary drum vacuum filter without rinsing. The destarched slurry was fed to the drum at 1.2 gal/min at a density of about 1.016 g/ml. The pH was as is, and estimated to be be about 5.9 based on typical analysis of the filter cake. Upon completion of the vacuum dewatering, the treated cake was frozen until it was ready for extraction.

98 kg of the untreated, destarched corn gluten cake with 60-65% moisture, which is in irregular flake form, was passed through a ¼-inch screen mounted on a Sweco shaker. This produced a more uniform particle to feed to the fluid bed dryer. The fluid bed dryer was fed at a rate of about 5.4 kg/hour, with inlet air temperatures of 120° C., bed temperature of 50° C. to obtain products of about 30-40% moisture content. The product recovered after drying was returned to refrigerated storage until extraction.

The cake was fed through a dual rotor crusher with 0.125-inch screen to generate a uniformly sized particle for homogenious extraction. The cake was fed into a Crown Iron Works Model IV immersion extractor using a drag conveyor dropping through a crossover screw and then a delumper (for a better understanding, and illustration of the Crown Iron Works Model IV immersion extractor may be found on the crowniron.com website) into the extractor. The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent steam. At the end of the conveyor, the solids dropped onto another conveyor with a similar arrangement. The model IV extractor has six extraction stages. Fresh solvent (98 wt % EtOH) then was supplemented with hydrogen peroxide to about 125 to 2000 ppm (see Table 6 for hydrogen peroxide concentrations). Solvent was introduced at the discharge end and flowed towards the inlet end and was ultimately discharged at a point preceeding the solids introduction. After the final solvent contact, the solids were conveyed up a long section to allow more extensive draining before falling into a crossover screw for transport to desolventizing. The solvent was fed into the system at a solvent:solids ratio of about 10 and the solvent was maintained at a temperature of about 25° C. Total contact time was about 30 minutes and the initial concentration of free sulfite in the unextracted material was 517 ppm of SO2.

TABLE 6

Hydrogen peroxide concentrations in the ethanol used to extract corn protein isolate products according to Example 11 and resulting residual free sulfite concentrations in the product.

| Sample ID (& percent protein) | PPM of Hydrogen Peroxide concentration in ethanol | Residual sulfite (ppm) as SO2 |
| --- | --- | --- |
| CPI-P-122716-181-3A (86.04 wt % protein) | 125 | 167 |
| CPI-P-122716-181-3B (87.62 wt % protein) | 250 | 158 |
| CPI-P-122716-181-4A (87.06 wt % protein) | 500 | 134 |
| CPI-P-122716-181-4B (86.70 wt % protein) | 1000 | 115 |
| CPI-P-122716-181-5A (85.94 wt % protein) | 2000 | 95 |

The resulting materials were desolventized in a screw desolventizer, operated with a surface temperature of about 95° C. and an absolute pressure of about −26 inches of Hg. To improve evaporation, a sweep of nitrogen gas is injected into the vapor space of the desolventizer and is allowed to flow to the vacuum discharge.

Example 12

Hydrogen Peroxide Treatment in the Pilot Drum and Pilot Extraction

Destarched corn gluten cake was collected on a rotary drum vacuum filter with rinsing. The destarched slurry was fed to the drum at 1.2 gal/min at a density of about 1.016 g/mL. The pH was as is, and estimated to be about 5.9 based on typical analysis of the filtered cake. The rinse water supplemented with active hydrogen peroxide at a concentration of 0.3% w/w was applied at 0.12 gal/min (Wash ratio=1/10). Upon completion of the vacuum dewatering, the treated cake was frozen until it was ready for extraction.

98 kg of the untreated, destarched corn gluten cake with 60-65% moisture, which is in irregular flake form, was passed through a ¼-inch screen mounted on a Sweco shaker. This produced a much more uniform particle to feed to the fluid bed dryer. The fluid bed dryer was fed at a rate of about 5.4 kg/hour, with inlet air temperatures of 120° C., bed temperature of 50° C. to obtain products of about 30-40% moisture content. The product recovered after drying was returned to refrigerated storage until extraction.

The cake was fed through a dual rotor crusher with 0.125-inch screen to generate a uniformly sized particle for homogeneous extraction. The cake was fed into a Crown Iron Works Model IV immersion extractor using a drag conveyor dropping through a crossover screw and then a delumper (for a better understanding, and illustration of the Crown Iron Works Model IV immersion extractor may be found on the crowniron.com website) into the extractor. The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent steam. At the end of the conveyor, the solids dropped onto another conveyor with a similar arrangement. The model IV extractor has six extraction stages. Fresh solvent was supplemented with hydrogen peroxide to about 350 ppm. Solvent was introduced at the discharge end and flowed towards the inlet end and was ultimately discharged at a point preceding the solids introduction. After the final solvent contact, the solids were conveyed up a long section to allow more extensive draining before falling into a crossover screw for transport to desolventizing. The solvent was fed into the system at a solvent:solids ration of about 10 and the solvent was maintained at a temperature of about 25° C. Total contact time was about 30 min.

The resulting materials were desolventized in a screw desolventizer, operated with a surface temperature of about 95° C. and an absolute pressure of about 26 inches of Hg. To improve evaporation a sweep of nitrogen gas is injected into the vapor space of the desolventizer and is allowed to flow to the vacuum discharge.

The resulting material had a residual SO2 of about 56 ppm.

The invention claimed is:
1. A method of treating a corn protein-rich stream, comprising:
providing a protein-rich stream derived from a wet corn milling operation, wherein the protein-rich stream comprises not less than 80% corn protein on a dry weight basis and comprises sulfite in a range of about 300 ppm to 5000 ppm on an as-is weight basis;

forming a wet cake by filtration of the protein-rich stream to provide a) a water-washed cake and b) a first filtrate;

subsequently spraying the water-washed cake with a hydrogen peroxide solution while maintaining filtration vacuum to provide a) a hydrogen peroxide treated cake and b) a second filtrate; and harvesting the hydrogen peroxide treated cake to obtain a corn protein product having a free sulfite concentration of less than 150 ppm on an as-is basis.

2. The method of claim 1, wherein the forming a wet cake step and the spraying step are carried out in the same filtration apparatus.

3. The method of claim 2, wherein the forming a wet cake step and the spraying step are carried out in a drum filtration apparatus.

4. The method of claim 1, wherein the sulfite level of total filtrate from the method does not change when the second filtrate is added to the first filtrate.

5. The method of claim 1, wherein the hydrogen peroxide solution is sprayed in an amount to apply from 1.8 moles to 10 moles of the hydrogen peroxide to oxidize 1 mole of free sulfite in the water-washed cake.

6. The method of claim 1, wherein the corn protein product has a free sulfite concentration of less than 20 ppm on an as-is basis.

7. The method of claim 1, wherein the corn protein product has a free sulfite concentration of less than 10 ppm on an as-is basis.

8. The method of claim 1, wherein the corn protein product comprises between about 90% and 98% corn protein on a dry weight basis.

9. The method of claim 1, wherein the corn protein product is for human and animal consumption.

10. The method of claim 1, wherein the protein-rich stream comprises greater than 85% corn protein on a dry weight basis.

11. The method of claim 1, wherein the corn protein product has a free sulfite concentration of less than 40 ppm on an as-is basis.

12. The method of claim 1, wherein the protein-rich stream comprises sulfite in a range of about 500 ppm to 900 ppm on an as-is weight basis.

* * * * *